US006579694B2

(12) United States Patent
Heifets et al.

(10) Patent No.: US 6,579,694 B2
(45) Date of Patent: Jun. 17, 2003

(54) **AGAR MEDIUM FOR THE GROWTH OF *MYCOBACTERIUM TUBERCULOSIS***

(75) Inventors: Leonid Heifets, Denver, CO (US); Tracy Sanchez, Lafayette, CO (US)

(73) Assignee: National Jewish Medical and Research Center, Denver, CO (US)

(*) Notice: Subject to any disclaimer, the term of this patent is extended or adjusted under 35 U.S.C. 154(b) by 35 days.

(21) Appl. No.: 09/812,986

(22) Filed: Mar. 20, 2001

(65) Prior Publication Data

US 2001/0055787 A1 Dec. 27, 2001

Related U.S. Application Data

(60) Provisional application No. 60/190,701, filed on Mar. 20, 2000.

(51) Int. Cl.[7] .................................................. C12Q 1/04

(52) U.S. Cl. .......................... 435/34; 435/391; 435/431

(58) Field of Search ............................. 435/29, 32, 34, 435/253.1, 391, 431

(56) References Cited

U.S. PATENT DOCUMENTS 5,643,723 A * 7/1997 Persing et al. ................. 435/6
6,168,930 B1 * 1/2001 Horn ........................... 435/34

OTHER PUBLICATIONS

Realini et al. (1999). Blood and charcoal added to acidified agar media to promote the growth of *Mycobacterium genavense*. Diagn Microbiol Infect Dis 34: 45–50.*

Pfyffer et al. (1999). Multicenter laboratory validation of susceptibility testing of *Mycobacterium tuberculosis* against classical second–line and newer antimicrobial drugs. J Clin Micr 37 (10): 3179–3186.*

Yajko et al. (1995). Colorimetric method for determining MICs of antimicrobial agents for *Mycobacterium tuberculosis*. J Clin Micr 33 (9): 2324–2327.*

Butler et al., *J. Clin. Microbiol.*, 16:1106–1109 (1982).

Butler et al., *Antimicrob Agents Chemother.*, 24:600–601 (1983).

Cohn et al., *Am. Rev. Respir. Dis.* 98:295–296 (1968).

Dorset, *Science*. 17:374 (1903).

Dubos, *Amer. Rev. Tuberc. Pulm. Dis.*, 56:334–345 (1947).

Harris, American Trudeau Society, *Handbook of Tuberculosis Laboratory Methods*, Washington, D.C. (1962).

Jensen, IUAT, *Bull Int Union Tuberc Lung Dis*. 24:78–112 (1954).

Jensen, *Abteilung Originale*. 125:222–239 (1932).

McClatchy et al., *Am. J. Clin. Pathol*, 65:412–415 (1976).

Middlebrook et al., *Amer. J. Publ. Health*, 48:844–853 (1958).

Mitchison et al., *J. Med. Microbiol.* 5:165–175 (1972).

Petragnani, *Bollettino dell'stituto sieroterapico Milanese*. 5:173–185 (1926).

Petroff, *J. Exp. Med.* 21:38–42 (1915).

Stonebrink, *Acta Tuberc. Scand.* 35:67–80 (1958).

* cited by examiner

*Primary Examiner*—Ralph Gitomer
(74) *Attorney, Agent, or Firm*—Sheridan Ross P.C.

(57) ABSTRACT

A novel agar medium for the isolation, sub-cultivation, and indirect or direct drug-susceptibility testing of *Mycobacterium tuberculosis* is disclosed. Also disclosed are methods of isolating and growing *Mycobacterium tuberculosis* and methods of drug-resistance screening using the agar medium of the invention.

23 Claims, No Drawings

AGAR MEDIUM FOR THE GROWTH OF *MYCOBACTERIUM TUBERCULOSIS*

CROSS-REFERENCE TO RELATED APPLICATIONS

This application claims the benefit of priority under 35 U.S.C. §119(e) from U.S. Provisional Application Ser. No. 60/190,701, filed Mar. 20, 2000, and entitled "New Agar Medium For *Mycobacterium tuberculosis*". The entire disclosure of U.S. Provisional Application Ser. No. 60/190,701 is incorporated herein by reference.

FIELD OF THE INVENTION

This invention relates to a novel agar medium for the isolation, sub-cultivation, and indirect or direct drug-susceptibility testing of *Mycobacterium tuberculosis*. The invention also relates to methods of isolating and growing *Mycobacterium tuberculosis* and to methods of drug-resistance screening using the agar medium of the invention.

BACKGROUND OF THE INVENTION

At first glance, it seems that nothing is new in the cultivation of *Mycobacterium tuberculosis*. The first attempts of *M. tuberculosis* cultivation on agar medium go back to the report by Fannie and Walter Hesse in 1881. In 1882, Robert Koch used blood serum coagulated on glass slides for *M. tuberculosis* cultivation. Apparently, he was not too much concerned about the biosafety of such a procedure. He later improved this method, which was called the "plate technique", by adding peptone, some salts and glycerol. Also, in 1882, Richard Petri invented the petri dish to be used instead of a glass slide. These attempts at cultivation on a transparent type of media were interrupted in 1903 with introduction of the first egg-based media by Dorset (Dorset, Science. 17:374, 1903), followed by a variety of egg-based media recipes (American Trudeau Society, *Handbook of Tuberculosis Laboratory Methods*, Washington, D.C., 1962; IUAT, *Bull Int Union Tuberc Lung Dis.* 24:78, 1954; Jensen, *Abteilung Originale.* 125:222–239, 1932; Ogawa et al., Kekkaku. 24:13–29, 1949; Petragnani, *Bollettino dell'Istituto sieroterapico Milanese.* 5:173–185,1926; Petroff, *J. Exp. Med.* 21:38–42, 1915; Stonebrink, *Acta Tuberc. Scand.* 35:67–80, 1958).

Based on systemic studies of the tubercle bacilli requirements, Dubos and Middlebrook in 1947 introduced the first effective agar medium under the name "Dubos Oleic Acid Albumin Agar" (Dubos, *Amer. Rev. Tuberc. Pulm. Dis.,* 56:334–345, 1947). It followed by an invention by Middlebrook and Cohn of the 7H10 agar in 1958 (Middlebrook et al., *Amer. J. Publ. Health,* 48:844–853, 1958) and 7H11 agar in 1968 (Cohn et al., *Am. Rev. Respir. Dis.* 98:295–296, 1968). Subsequently, two recipes of a selective agar medium containing four antimicrobials to prevent the growth of contaminants (PolymyxinB, AmphotericinB, Carbenicillin, Trimethoprim) were introduced in 1972 (Mitchison et al., *J. Med. Microbiol.* 5:165–175, 1972) and in 1976 (McClatchy et al., *Am. J. Clin. Pathol.* 65:412–415, 1976). A powder base for all these media, 7H10 agar, contains agar, combination of seven salts, L-glutamic acid, pyridoxine, biotin, malachite green. It is available commercially from a number of manufacturers. Preparation of an agar medium requires addition of the OADC growth supplement, which contains sodium oleate, albumin (bovine, fr. V) dextrose, catalase.

At the time the 7H10 and 7H11 agar media were developed by Middlebrook and his colleagues working at the National Jewish Hospital in Denver, Colo., attempts to use an animal serum as a nutritional supplement failed because of inconsistent results with different serum batches. Therefore, a combination of the only standardized products available at that time, sodium oleate with bovine albumin, were used as the major component of the OADC supplement. The role of the bovine albumin is to neutralize the oleic acid, which is toxic to mycobacteria, in case of breakdown of sodium oleate. This composition required a final pH of 6.8, in spite of the known fact that the optimal pH for *M. tuberculosis* is 6.2–6.4. Subsequently, the presence of 5–7% of $CO_2$ in the incubator is required to protect the growing mycobacteria from further alkalization of the environment due to the release of ammonia by the growing mycobacteria. Until the time of the present invention, these culture conditions remained the standard in the art.

The agar-based medium developed by Middlebrook and colleagues has a number of advantages over egg-based medium. One of them is transparency, which enables earlier detection of growing colonies. Among the major disadvantages of the existing agar media are the cost, difficulties in standardization of the OADC supplement, and the need for a $CO_2$ incubator. These disadvantages represented the main obstacle in implementing the agar media outside of the US, especially in developing countries.

Timely identification of patients with drug resistance, especially those with multi-drug resistant tuberculosis (MDR-TB), is a key element of any comprehensive program targeting prevention of epidemics of drug-resistant tuberculosis. Drug susceptibility testing of the patients' isolates as a means to address this problem in developing countries has been considered impractical and unrealistic. A number of reasons for this, real or fictional, have been given by different authors, such as extreme sophistication of the procedure, high cost, and extended turnaround time for laboratory reports.

Pyrazinamide (PZA) is one of the first-line drugs in the standard treatment regimen currently used for tuberculosis patients. It is now mandatory in the United States (man. 12), and it is desirable for any country with high prevalence of drug resistance (man. 3) to perform a drug susceptibility test for pretreatment isolates from all new tuberculosis patients, at least with the first-line drugs. A variety of techniques can be used for susceptibility testing with any of the anti-tuberculosis drugs other than PZA, including the agar proportion method in its direct or indirect versions. However, the only approved test using PZA in the United States is the radiometric method using the special PZA liquid medium with pH 6.0 in the BACTEC-460 system (man. 10). This method is quite expensive and may not be affordable for many laboratories, especially in developing countries. In addition, the method requires the disposal of a substantial volume of $^{14}C$-radiolabeled culture vials, which is not permitted in many countries. Further, the test is not fully standardized and may give false-positive and false-negative results (man. 4–6). Unlike the agar proportion method test for other anti-tuberculosis drugs, the test in a liquid medium does not provide any information on the actual proportion of the PZA-resistant bacteria in the patient's bacterial population, and it cannot be used as a direct test (i.e., a pure culture must be isolated from the patient sample prior to testing). Therefore, the total turnaround time of the method is about four weeks, at best. There has been a suggestion to use the agar proportion method for PZA by substituting an ADC supplement for the conventional OADC supplement in a pH 5.5 agar medium (man. 1, 2). However, this revised method did not find its way into the clinical laboratory practice because of very poor growth of *Mycobacterium tuberculosis* isolates a pH 5.5 in the conventional agar medium (man. 11). Therefore, while a number of alternative methods for susceptibility testing with other drugs are widely available, the BACTEC method remains the only reliable technique for a test with PZA. Moreover, PZA only works at an acidic pH, which alone can inhibit the growth of *M. tuberculosis* on conventional medium.

Therefore, prior to the present invention, there was a need for a new agar medium, which does not require sophisticated or expensive cultivation techniques, which can be produced at a lower cost, and which can be used for susceptibility/resistance screening of *Mycobacterium tuberculosis* isolates against a wide range of drugs, including Pyrazinamide, with a reasonable turnaround time.

SUMMARY OF THE INVENTION

The present invention generally relates to a novel agar medium for the isolation, growth and screening of *Mycobacterium tuberculosis*. The agar medium includes: (a) an agar base suitable for growth of *Mycobacterium tuberculosis*; and, (b) animal serum at a concentration of between about 8% and 12% of the final volume of the agar medium. The medium is at a pH of between about 6.0 to about 6.25. Preferably, the agar base is selected from the group consisting of Middlebrook and Cohn 7H10 and Middlebrook and Cohn 7H11.

The animal serum can be any suitable animal serum including, but not limited to, bovine fetal calf serum, calf serum, bovine serum, equine fetal calf serum and equine serum. In one embodiment, the animal serum is at a concentration of between about 8% and 12% of the final volume of the agar medium; in another embodiment, the animal serum is at a concentration of between about 9% and 11% of the final volume of the agar medium; in another embodiment, the animal serum is at a concentration of about 10% of the final volume of the agar medium.

Preferably, the medium is at a pH of between about 6.0 to about 6.25, and another one embodiment, the medium of is at a pH of between about 6.0 to about 6.2; in another embodiment, the medium is at a pH of between about 6.1 and 6.2; and in another embodiment, the medium is at a pH of about 6.1.

The agar medium can include a mixture of antimicrobial agents comprising polymixin B, carbenicillin, amphotericin B, and trimethoprim lactate. In one aspect, the antimicrobial agents are present at a final concentration of: 200 units/ml polymyxin B, 10 $\mu$g/ml amphotericin B, 50 $\mu$g/ml carbenicillin, and 20 $\mu$g/ml trimethoprim.

In one aspect, the medium further comprises an amount of at least one drug effective for the identification of *Mycobacterium tuberculosis* organisms that are susceptible or resistant to the drug. Such a drug can include, but is not limited to, isoniazid, streptomycin sulfate, di-hydro-streptomycin, rifampin, pyrazinamide, ethambutol, etionamide, capreomycin sulfate, amikacin, kanamycin sulfate, levofloxacin, p-aminosalicylic acid, D-cycloserine, and/or clofazimine. In one aspect, the drug comprises isoniazid and rifampin, wherein each of the drugs is isolated within a segment of the agar medium. In a preferred embodiment, the isoniazid is present in two segments of the agar medium, and wherein each segment contains a different concentration of the isoniazid. In another aspect, the drug is includes: isoniazid, rifampin, pyrazinamide and either of streptomycin sulfate or di-hydro-streptomycin, wherein each of the drugs is isolated within a different segment of the agar medium. In another aspect, the drug comprises: ethambutol, etionamide, levofloxacin, capreomycin sulfate, and either of amikacin or kanamycin sulfate, wherein each of the drugs is isolated within a different segment of the agar medium. In yet another aspect, the drug comprises: p-aminosalicylic acid, D-cycloserine, and clofazimine, wherein each of the drugs is isolated within a different segment of the agar medium. In another aspect, the drug comprises pyrazinamide.

Yet another embodiment of the present invention relates to a method for culturing *Mycobacterium tuberculosis*, comprising inoculating an agar medium with a sample containing *Mycobacterium tuberculosis*. The agar medium is the agar medium as set forth above. In one aspect, the medium further comprises a mixture of antimicrobial agents comprising polymixin B, carbenicillin, amphotericin B, and trimethoprim lactate. Preferably, the antimicrobial agents are incorporated into one half of the agar medium in a plate, and the other half of the agar medium in the plate does not contain the antimicrobial agents. In this aspect, the agar medium is inoculated with an undiluted sample obtained from a patient, although the sample can be diluted, for example, by at least about 10 fold. In one aspect, the sample is a previously isolated sample of *Mycobacterium tuberculosis*.

Another embodiment of the present invention relates to a method for testing the drug susceptibility of a culture of *Mycobacterium tuberculosis*. This method includes the steps of: (a) inoculating an agar medium as set forth above, with a sample containing *Mycobacterium tuberculosis*, wherein the agar medium further comprises an amount of at least one drug effective for selection against *Mycobacterium tuberculosis* organisms that are susceptible to the drug; (b) incubating the inoculated agar medium for a time sufficient to detect growth of the *Mycobacterium tuberculosis* in the absence of a growth-inhibiting drug; and, (c) measuring growth of the *Mycobacterium tuberculosis* on the agar medium as compared to growth of the *Mycobacterium tuberculosis* on the agar medium in the absence of the at least one drug. A growth rate of the *Mycobacterium tuberculosis* on the agar medium containing the at least one drug that is less than a pre-established drug-resistance level for the at least one drug, when compared to the growth rate of the *Mycobacterium tuberculosis* on the agar medium in the absence of the at least one drug, indicates that the *Mycobacterium tuberculosis* is susceptible to the at least one drug. In one aspect, the pre-established drug-resistance level is 1%, and wherein a growth rate of the *Mycobacterium tuberculosis* on the agar medium containing the at least one drug that is less than 1% of the growth rate of the *Mycobacterium tuberculosis* on the agar medium in the absence of the at least one drug, indicates that the *Mycobacterium tuberculosis* is susceptible to the at least one drug. In another aspect, the at least one drug is pyrazinamide, wherein the pre-established drug-resistance level is 10%, and wherein a growth rate of the *Mycobacterium tuberculosis* on the agar medium containing the pyrazinamide that is less than 10% of the growth rate of the *Mycobacterium tuberculosis* on the agar medium in the absence of the pyrazinamide, indicates that the *Mycobacterium tuberculosis* is susceptible to pyrazinamide.

Preferably, the step of incubating is for a time of at least about 3 weeks. In one aspect, the step of incubating is for a time of from between about 3 weeks and about 6 weeks. Preferably, the step of incubating is performed in the absence of supplemental $CO_2$.

The drug to be added to the agar medium can include, but is not limited to, isoniazid, streptomycin sulfate, di-hydrostreptomycin, rifampin, pyrazinamide, ethambutol, etionamide, capreomycin sulfate, amikacin, kanamycin sulfate, levofloxacin, p-aminosalicylic acid, D-cycloserine, and/or clofazimine. In one aspect, the medium comprises the drugs isoniazid and rifampin, and each of the drugs is isolated within a different segment of the agar medium. In this aspect, the isoniazid is preferably present in two different segments of the agar medium, and wherein each segment contains a different concentration of the isoniazid. In this aspect, the agar medium can be directly inoculated with a sample collected from a patient. In one embodiment, the sample is undiluted. In another embodiment, the agar medium is inoculated with a sample diluted by at least 10 fold.

In another aspect of this method, the agar medium comprises the drugs: isoniazid, rifampin, pyrazinamide and either of streptomycin sulfate or di-hydro-streptomycin, and each of the drugs is isolated within a different segment of the agar medium. In this aspect, the agar medium is preferably inoculated with a previously isolated culture of *Mycobacterium tuberculosis* from a sample obtained from a patient.

In another aspect of this method, the medium comprises the drugs: ethambutol, etionamide, levofloxacin, capreomycin sulfate, and either of amikacin or kanamycin sulfate, and each of the drugs is isolated within a different segment of the agar medium. In this aspect, the agar medium is preferably inoculated with a previously isolated culture of *Mycobacterium tuberculosis* from a sample obtained from a patient.

In another aspect of this method, the medium comprises the drugs: p-aminosalicylic acid, D-cycloserine, and clofazimine, and wherein each of the drugs is isolated within a different segment of the agar medium. In this aspect, the agar medium is preferably inoculated with a previously isolated culture of *Mycobacterium tuberculosis* from a sample obtained from a patient.

In yet another aspect of this method, the agar medium comprises the drug, pyrazinamide.

DETAILED DESCRIPTION OF THE INVENTION

The present inventors disclose herein a novel agar medium and methods of using such a medium. The medium is generally referred to herein as HSTB agar medium. The agar medium is useful for the isolation of *Mycobacterium tuberculosis* from patient specimens, for the sub-cultivation of *Mycobacterium tuberculosis* pure cultures, and for direct and indirect drug susceptibility testing against *Mycobacterium tuberculosis*. The agar medium of the present invention has the following advantages over prior agar mediums for the culture of *M. tuberculosis*: (1) it an be used in regular incubators in the absence of supplemental $CO_2$, because the medium has an acidic pH of 6.0–6.25, and because it uses an animal serum instead of the OADC that was conventional in this type of medium prior to the present invention; (2) it can be used for testing susceptibility to pyrazinamide (PZA) because it has a lower pH than conventional media (PZA requires lower pH), enabling the testing of PZA in combination with other tuberculosis (TB) drugs on the same plate; and, (3) it is much less expensive than conventional agar mediums for *M. tuberculosis* because the conventional OADC supplement is replaced with an animal serum.

More particularly, the present inventors have demonstrated that the agar medium of the present invention, HSTB agar, supports growth of *M. tuberculosis* in regular incubators, without supplemental $CO_2$ in the atmosphere. This feature makes this medium more acceptable than the conventional Middlebrook 7H10/7H11 agar in settings where installation of $CO_2$ incubators, as in many developing countries, may represent a problem. Another advantage of the HSTB agar over the conventional 7H 10/7H11 agar is that it contains animal serum instead of OADC, which makes it easier to standardize and lower in cost. The present inventors have introduced the use of HSTB in two settings: one is a bi-plate containing plain and selective HSTB agar (i.e., HSTB agar in the presence of antimicrobial agents for the isolation of *M. tuberculosis* cultures), another is a multi-segmented plate containing plain agar, as well as an agar with various drugs for direct and indirect susceptibility testing of *M. tuberculosis*-containing samples and previously isolated *M. tuberculosis* cultures. The present inventors have demonstrated that HSTB was more efficient than 7H11 agar and all other media tested (L-J slant, BACTEC and MGIT broth) in recovery from sputum specimens evaluated. Moreover, the present inventors have demonstrated the ability to determine critical concentrations of TB drugs using the HSTB agar of the present invention. The concentrations could clearly separate resistant and susceptible strains, could distinguish low and high levels of isoniazid (INH) resistance, and could detect resistance in cultures containing various proportions of resistant bacteria—100%, 50%, 10%, 1%. Results of an indirect test on HSTB and 7H10/7H11 agar were reportable in three weeks for more than 80% strains, as compared to a turnaround time for a test in liquid MGIT medium of two weeks for 41% cultures and an additional 37% after the third week. The advantage of the test on agar medium is that it gives an actual proportion of resistant bacteria in the isolate, is more sensitive in detecting small proportions of resistant bacteria in the culture, and is applicable to both first- and second-line drugs. Finally, the cost of three quadrant HSTB agar plates with 11 drugs (including PZA) is about two-fold less than 7H110 agar, and 10–15 fold less than MGIT tubes for a test with four or five drugs only.

The present inventors have further shown that the HSTB agar medium of the present invention can be used for susceptibility testing of *M. tuberculosis* isolates with pyrazinamide by an agar proportion method. This test is less expensive than the conventional testing with PZA in the liquid BACTEC system, the medium can be used in both an indirect test with previously isolated cultures and in a direct test method with acid fast bacilli (AFB)-positive sputum specimens, and the total turnaround time (from the moment the patient's specimen is obtained) can be as short as three weeks for at least 85% of the AFB-positive specimens.

Accordingly, one embodiment of the present invention relates to an agar medium, comprising: (a) an agar base suitable for growth of *Mycobacterium tuberculosis*; and, (b) animal serum at a concentration of between about 8% and 12% of the final volume of the agar medium. The medium is at a pH of between about 6.0 to about 6.25. As discussed above, the novel agar medium of the present invention can also be referred to herein as HSTB agar.

One essential component of the agar medium of the present invention is the agar base of the medium. According to the present invention, an agar base that is suitable for the growth of *Mycobacterium tuberculosis* can be any agar base that contains basic ingredients which will support the growth of *Mycobacterium tuberculosis* (pure cultures or specimens containing *Mycobacterium tuberculosis*), when such base is supplemented with a suitable growth supplement (e.g., animal serum, according to the present invention, or OADC or ADC according to conventional recipes). Typically, the agar base is provided as a powder base, and therefore is hydrated for use. To prepare the agar medium, the agar base is hydrated, supplemented with the growth supplement, and adjusted to the desired pH, for example by the addition of one or more salts, such as monopotassium phosphate ($KH_2PO_4$). Additional ingredients can be added as desired, such as glycerol as an additional nutritional component, although such ingredients are not considered to be essential ingredients of the agar medium. In addition, as discussed below, various antimicrobial agents and tuberculosis drugs can be incorporated into the medium for the purpose of isolating *M. tuberculosis* cultures and for drug susceptibility testing. Currently, there are two agar bases that are particularly suitable for use in the agar medium of the present invention, Middlebrook and Cohn 7H10 agar (also referred to as "7H10 agar" or "7H10") and Middlebrook and Cohn 7H11 agar (also referred to as "7H11 agar" or "7H11"). 7H11 is 7H10 agar with the addition of pancreatic digest of casein. It is available commercially through several manufacturers (e.g., BBL). These media have been described in detail by Middlebrook and colleagues (e.g., Middlebrook et al., *Amer. J. Publ. Health,* 48:844–853, 1958; Cohn et al., *Am. Rev. Respir. Dis.* 98:295–296, 1968) and represent the art standard agar bases for the culture of *Mycobacterium tuberculosis*. The powder base, 7H10 agar, contains agar, combination of seven salts, L-glutamic acid, pyridoxine, biotin, malachite green. It is available commercially from a number of manufacturers. It is to be understood that variations of the conventional 7H10/7H11 agar bases could be derived by one of skill in the art, and it is contemplated that such agar bases could be used in the agar medium of the present invention.

One essential feature of the agar medium of the present invention is the pH of the medium. Prior to the present invention, the conventional agar media for *M. tuberculosis* were required to be formulated at a pH of 6.8, despite the knowledge that the optimal pH for *M. tuberculosis* is 6.2–6.4. Attempts to alter the conventional agar media to a pH of 5.5 by the substitution of ADC for the conventional supplement, OADC, resulted in very poor growth of the *M. tuberculosis* on the medium. However, the first-line tuberculosis drug, pyrazinamide, only works at acidic pH and has not previously been successfully used in an agar medium for *M. tuberculosis* drug susceptibility testing. The present inventors have demonstrated that the combination of an acidic pH with the use of animal serum in the agar medium produces an agar medium that is more efficient than 7H10/7H11 agar and all other media tested (L-J slant, BACTEC and MGIT broth) in recovery of *M. tuberculosis* from patient specimens, and allows for the first time the testing for PZA susceptibility in an agar medium, alone or in conjunction with the testing of other tuberculosis drugs. According to the present invention, the pH of the agar medium is between about pH 6.0 and about pH 6.25, and in another embodiment, between about pH 6.0 and pH 6.2, and in another embodiment, between about pH 6.1 and pH 6.2, and in another embodiment, is about pH 6.1. The use of the term "about" with regard to the pH of the medium refers can refer to a variance of up to 0.1 in either direction (i.e., "about 6.0" can include a pH of 5.9 and 6.1). The pH of the medium is adjusted to the desired pH by any suitable method as is well known in the art, including by the addition of one or more acids or bases to the medium, which are typically provided in the form of a salt.

Another essential feature of the agar medium of the present invention is the use of an animal serum at a concentration of from about 8% to about 12% of the final volume of the medium. As discussed above, prior attempts to use an animal serum as a nutritional supplement in agar medium for *M. tuberculosis* failed because of inconsistent results with different serum batches. Therefore, a combination of standardized products, sodium oleate with bovine albumin, was developed and used as the major component of the OADC supplement. The role of the bovine albumin is to neutralize the oleic acid, which is toxic to mycobacteria, in case of breakdown of sodium oleate. This composition required a final pH of 6.8, which, as described above, is not optimal for the growth of *M. tuberculosis*, and prevented the testing for susceptibility to the first-line drug, pyrazinamide. The present inventors have now discovered that the use of animal serum in place of the conventional OADC supplement allows for the growth of *M. tuberculosis* on the agar medium at a much lower pH, and further allows for the testing of tuberculosis drugs in an agar setting which require acidic pH (e.g., PZA). According to the present invention, the animal serum can be any animal serum, or a synthetic variant of an animal serum, that can readily be incorporated into a medium. Preferred animal sera include, but are not limited to, fetal bovine serum, calf bovine serum, bovine serum, fetal equine serum, and equine serum. As discussed above, the serum is added to the medium at a final concentration of about 8% to about 12% of the final volume of the medium. Preferably, the serum is added at a final concentration of from about 9% to about 11%, and more preferably, at about 10%. As used with regard to the concentration of serum in the medium, the term "about" can include a variance of 1% in either direction, even though the target concentration is the stated concentration (e.g., "about 10%" can include 9% and 11%).

In one embodiment of the present invention, the HSTB agar can additionally include one or more antimicrobial agents, which are added to prevent the growth of contaminants on the medium, thereby enhancing the usefulness of the medium for isolating cultures of *Mycobacterium tuberculosis*. According to the present invention, HSTB agar that contains antimicrobial agents to prevent the growth of contaminants can be referred to as "selective HSTB agar". Typically, the selective HSTB is used to isolate *M. tuberculosis* cultures from a patient's specimen (e.g., a sputum specimen). Selective HSTB can also be used as one type of control plate alongside a separate plate containing a tuberculosis drug that is used for direct susceptibility testing of a sample from a patient. As used herein, the term "antimicrobial agent" is generally intended to refer to any agent (i.e., a drug) that will inhibit the growth of microorganisms other than *Mycobacterium tuberculosis*, but which do not substantially inhibit the growth of the *M. tuberculosis*. Therefore, in the present invention, reference to an antimicrobial agent is generally not intended to refer to the tuberculosis drugs that are used in susceptibility testing. Antimicrobial agents for use in the agar medium of the present invention include any agent that inhibits the growth of a microorganisms (including bacteria, fungi, viruses, and other mycobacteria) other than *Mycobacterium tuberculosis*, but which do not substantially inhibit the growth of the *M. tuberculosis*. Preferred antimicrobial agents for use in a selective agar medium of the present invention include, but are not limited to, polymixin B, carbenicillin, amphotericin B, and trimethoprim lactate. In one embodiment, the antimicrobial agents are present at a final concentration of: 200 units/ml polymyxin B, 10 $\mu$g/ml amphotericin B, 50 $\mu$g/ml carbenicillin, and 20 $\mu$g/ml trimethoprim. It is to be understood, however, that it is well within the ability of one of skill in the art to alter these concentrations as desired to inhibit the growth of contaminants on the medium.

Typically, the antimicrobial agents are not used together in the medium with a tuberculosis drug for susceptibility testing. Instead, a separate plate, segment of a plate or well containing the antimicrobial agent(s) is used alongside (in addition to) a plate, segment of a plate or well that contains the tuberculosis drug. An example of a bi-plate containing plain HSTB medium on one half (one segment), and selective HSTB in the other half, is described below.

One embodiment of the present invention includes the HSTB agar medium of the present invention (described above) which additionally contains one or more drugs that are used to test *Mycobacterium tuberculosis* for susceptibility to the drug. Such drugs can include any drug that has been or will be identified as suitable for the inhibition of growth or the destruction of *Mycobacterium tuberculosis*, and are therefore potentially useful for the treatment of tuberculosis. Such drugs can also be referred to herein as "tuberculosis drugs".

Since some strains of *Mycobacterium tuberculosis* are resistant to some tuberculosis drugs, it is desirable to test a sample containing *M. tuberculosis* from a patient with tuberculosis against a variety of drugs, including various doses of some drugs, in order to evaluate and select one or more drugs and doses that will be best for use in the patient. Therefore, the present invention includes the incorporation of any tuberculosis drug into the agar medium of the present invention for the purpose of testing a sample of *M. tuberculosis* for susceptibility to the drug. Such drugs include, but are not limited to, isoniazid (INH), streptomycin sulfate (SM), di-hydro-streptomycin (SM), rifampin (RMP), pyrazinamide (PZA), ethambutol (EMB), etionamide (ETA), capreomycin sulfate (CM), amikacin (AK), kanamycin sulfate (KM), levofloxacin, p-aminosalicylic acid (PAS), D-cycloserine (CS), and clofazimine (CF).

The drugs to be tested for susceptibility are typically prepared as working stocks as described in detail in the exemplary protocols below, and are added to the medium with the animal serum before the agar has completely cooled and solidified. For the susceptibility testing is desirable to have a control medium which does not contain any drugs (i.e., plain HSTB or drug-free HSTB), and in some cases, a plate for isolation and/or control (for direct testing procedures) that contains just the antimicrobial drugs (i.e., selective HSTB). To provide the HSTB or selective HSTB, one option is to prepare additional plates containing the various agar medium types to be used alongside the plates containing the HSTB with the tuberculosis drugs. In a preferred embodiment, however, a single plate is segmented such that one portion of the plate can contain plain HSTB agar, and other portions of the plate can contain selective HSTB agar or HSTB agar containing a tuberculosis drug. In this manner, it is possible to prepare bi-plates (i.e., plates having two segments, one with plain HSTB agar medium and one with selective or drug-containing HSTB agar medium), as well as multi-segmented plates (i.e., plates having three, four, five, six, or more segments: one with plain HSTB agar, and each of the other segments with selective or drug-containing HSTB agar medium, wherein each of the other segment contains a different tuberculosis drug, or a different dose of the same tuberculosis drug). Segmented plates are available commercially and contain dividers within a single plate so that various types of medium can be poured into individual segments of the plate without cross-contaminating other segments. Alternatively, one can use a plate containing several different wells, wherein each well is filled with agar medium of a different type. Such culture plates are also available commercially.

In one embodiment, the HSTB agar medium of the present invention contains one, two or a few different drugs, wherein each of the drugs is added to a portion of the HSTB agar medium and then plated into a separate plate, separate well, or separate segment of a segmented plate so that the drugs can be tested in one experiment against the same inoculum. In one embodiment, the drugs are isoniazid or rifampin, wherein each of the drugs is isolated within a segment of the agar medium on a single plate, or within agar medium contained in separate wells in a multi-well plate. In a preferred aspect of this embodiment, the isoniazid is present in two segments of the agar medium, wherein each segment (or well of a multi-well plate) contains a different concentration of isoniazid (e.g., a high dose and a low dose). Preferably, another segment or well contains drug-free HSTB agar medium. In another embodiment, the HSTB agar medium of the present invention contains the drug, pyrazinamide, wherein the pyrazinamide is isolated within a segment of the agar medium on a single plate, and wherein the other segment of the medium is drug-free (plain agar). Any of the tuberculosis drugs disclosed herein are suitable for direct susceptibility testing, wherein a sample taken from a patient (e.g., a sputum sample) is directly inoculated onto the agar medium (i.e., without isolating the *M. tuberculosis* from the specimen first). It is to be noted, however, that any of the drugs disclosed herein can also be used in indirect susceptibility testing (i.e., wherein the sample is a culture of *M. tuberculosis* that has previously been isolated from a patient sample, such as by culturing on a selective HSTB agar medium of the present invention).

In another embodiment, the HSTB agar medium of the present invention contains combinations of several different drugs, wherein each of the drugs is added to a portion of the HSTB agar medium and then plated into a separate plate, separate well, or separate segment of a segmented plate, so that the drugs can be tested in one experiment against the same inoculum. In one exemplary embodiment, the drugs to be included in a single segmented plate include: isoniazid, rifampin, pyrazinamide and either of streptomycin sulfate or di-hydro-streptomycin, and wherein each of said drugs is isolated within a different segment of said agar medium. In another exemplary embodiment, the drugs to be included in a single segmented plate include: ethambutol, etionamide, levofloxacin, capreomycin sulfate, and either of amikacin or kanamycin sulfate, and wherein each of said drugs is isolated within a different segment of said agar medium. In yet another exemplary embodiment, the drugs to be included in a single segmented plate include: p-aminosalicylic acid, D-cycloserine, and clofazimine, and wherein each of said drugs is isolated within a different segment of said agar medium. These combinations of drugs are particularly suitable for indirect testing of patient samples (i.e., the patient sample is first cultured, for example on selective HSTB, to isolate the *M. tuberculosis*, and is then inoculated onto the susceptibility testing medium). It is to be understood that these combinations of drugs to be tested together are merely exemplary in nature; it is well within the ability of one of skill in the art to design different combinations of tuberculosis drugs for testing against a patient sample. Therefore, the present invention contemplates the use of any one of the above-identified tuberculosis drugs, alone or in combination with any one or more of the others of the above-identified tuberculosis drugs or with any other tuberculosis drug that has been or will be identified, in the agar medium of the present invention, for the purpose of direct or indirect susceptibility testing. It is an advantage of the agar medium of the present invention that drugs that must be used in an acidic environment (e.g., pyrazinamide) can be used in the same screening with other drugs that do not have such requirements.

The amount of a given drug to incorporate into a given volume of the agar medium of the present invention can be readily determined by those of skill in the art. This amount is typically determined by experimentally determining the critical concentration of a given drug in the HSTB medium, by measuring the highest MICs of the tuberculosis drug for strains that are known to be susceptible to the drug, and the lowest MICs for clinical isolates that are known to be resistant to the drug. Ideally, the critical concentration of a drug is the concentration at which the majority of the drug-susceptible strains are inhibited, while the majority of the drug-resistant strains can grow. Based on the critical concentration of drug in the medium, one can then determine the drug-resistance growth level or breakpoint, to be used when screening unknown cultures for drug susceptibility on the given drug (i.e., the percentage of growth on the drug as compared to in the absence of the drug, above which a culture is considered to be resistant to the drug). The determination of the critical concentrations of INH and RMP on HSTB is exemplified in Example 3. The determination of the critical concentration for PZA is exemplified in Example 5.

One embodiment of the present invention relates to a method for culturing *Mycobacterium tuberculosis*. The method comprises inoculating an agar medium of the present invention with a sample containing *Mycobacterium tuberculosis*. The agar medium can be the plain HSTB agar medium of the present invention as described above, the selective HSTB medium, or any tuberculosis drug-containing HSTB agar medium as described above. Methods for the inoculation of an agar medium are well known in the art, and include smearing, pipetting or pouring a sample onto the top of the agar medium and allowing the liquid in the sample to absorb into the surface of the medium. The sample containing the *Mycobacterium tuberculosis* can include any suitable sample, including an undiluted sample obtained directly from the patient (e.g., a sputum sample), a diluted sample obtained directly from the patient, or a culture of *Mycobacterium tuberculosis* that has been isolated previously from a patient sample. In one embodiment, sputum specimens are processed by the NaOH-NALC method with pH neutralization using a proper concentration procedure (described in detail below). If the specimen is to be diluted, the proper dilution can be determined by those of skill in the art. Standard dilutions include a two-fold dilution, a three-fold dilution, a four-fold dilution, a five-fold dilution, a ten-fold dilution, a one hundred-fold dilution, a one thousand-fold dilution, or a ten thousand-fold dilution.

Another embodiment of the present invention relates to a method for testing the drug susceptibility of a culture of *Mycobacterium tuberculosis*. The method includes the steps of: (a) inoculating an agar medium of the present invention with a sample containing *Mycobacterium tuberculosis*, wherein the agar medium contains an amount of at least one drug effective for selection against *Mycobacterium tuberculosis* organisms that are susceptible to the drug; (b) incubating the innoculated agar medium for a time sufficient to detect growth of the *Mycobacterium tuberculosis* in the absence of a growth-inhibiting drug; and, (c) measuring growth of the *Mycobacterium tuberculosis* on the agar medium as compared to growth of the *Mycobacterium tuberculosis* on the agar medium in the absence of the at least one drug. A growth rate of the *Mycobacterium tuberculosis* on the agar medium containing the at least one drug that is less than a pre-established drug-resistance level for the at least one drug, when compared to the growth rate of the *Mycobacterium tuberculosis* on the agar medium in the absence of the at least one drug, indicates that the *Mycobacterium tuberculosis* is susceptible to the at least one drug.

The agar medium of the present invention and drugs contained therein, including suitable formats for presenting the drugs for screening, have been described in detail above. The types of samples suitable for screening and the method of inoculation of the medium has also been described above. The step of incubating typically occurs at a temperature of from about 35–37° C., typically in the dark, and can be performed in the absence of supplemental $CO_2$ (i.e., in normal air conditions). In one embodiment, the step of incubating occurs for at least 2 weeks, and preferably about 3 weeks, and is typically from about 3 weeks to about 6 weeks. An incubation of longer than 6 weeks is typically undesirable, since after 6 weeks, typically represents the limit for interpretation of the drug susceptibility test results. In one embodiment, the sample can be initially cultured in a liquid medium, for example a Bactec vial, a MGIT tube, or a Redox tube, etc., which may shorten the turnaround time of the laboratory report and increase the overall rates of culture recovery. After recovery from the liquid medium, the culture is plated on the agar medium of the present invention, which may result in shorter incubation times. Of course, the incubation period can be adjusted and monitored readily by those of skill in the art.

The final step in this method includes measuring the growth of the *Mycobacterium tuberculosis* on the agar medium as compared to growth of the Mycobacterium tuberculosis on the agar medium in the absence of the at least one drug. Techniques for measuring the growth of *Mycobacterium tuberculosis* on the agar medium of the present invention include, but are not limited to, counting colonies on the plate under a microscope (e.g., a dissecting microscope). Typically, the number of colonies in a drug-containing segment or well is divided by the number of colonies grown on the drug-free control segment or well and multiplied by 100. If the percentage is greater than, or equal to, a pre-established drug-resistance level for the particular drug, then the culture is considered to be resistant to that drug. If the percentage is less than the pre-established drug-resistance level, then the culture is considered to be susceptible to that drug.

A pre-established drug-resistance level is a level of growth of a culture which represents the "break point" between a culture being resistant to the drug or susceptible to the drug. As described above, a critical concentration of a given drug can be determined for the drug in the agar medium of the present invention (e.g., see Examples 3 and 5). The drug-resistance level of growth is established by determining a percentage of growth on the critical concentration of the drug, as compared to the growth in the absence of the drug (i.e., 100%), below which the culture is considered to be susceptible to the drug. The drug-resistance level, or breakpoint, for certain of the tuberculosis drugs listed herein in HSTB agar medium has been determined by the present inventors, or can readily be determined, by those of skill in the art. For all of the tuberculosis drugs disclosed herein, with the exception of pyrazinamide, the pre-established drug-resistance level of growth is 1% (these are international standards). Therefore, for testing on these drugs, if the growth rate of the *Mycobacterium tuberculosis* on the agar medium containing the drug is less than 1% of the growth rate of the *Mycobacterium tuberculosis* on the agar medium in the absence of the drug, the sample of

*Mycobacterium tuberculosis* is susceptible to the drug. The breakpoint for pyrazinamide is 10% (this is an international standard). Therefore, for testing on pyrazinamide, if the growth rate of the *Mycobacterium tuberculosis* on the agar medium containing the pyrazinamide is less than 10% of the growth rate of the *Mycobacterium tuberculosis* on the agar medium in the absence of pyrazinamide, then the *Mycobacterium tuberculosis* is susceptible to pyrazinamide. The breakpoint, or pre-established drug-resistance growth rate, for other drugs can be determined by those of skill in the art using the guidance provided herein. If growth is present on the drug-containing media, the colonies must be counted. Over-inoculation may result in a false resistant interpretation.

In a preferred embodiment, a quality control strain of *Mycobacterium tuberculosis* which has previously been characterized against the drugs to be tested is included on a duplicate set of plates so that the quality of the plates can be confirmed. The following discussion provides further guidance on the preparation and use of the HSTB agar medium of the present invention. It is to be understood, however, that the protocols are to be considered to be exemplary, and that one of skill in the art, given the discussion herein, will be able to make modifications to the protocols as desired. Such variations that result in an agar medium or method that falls within the scope of the present claims is considered to be part of the present invention.

General Design of Plates Using HSTB Agar Medium

In general, three different types of plates are of interest for the isolation, sub-cultivation, and direct or indirect drug susceptibility testing of *Mycobacterium tuberculosis*: (1) whole plates containing plain HSTB agar (e.g., 20.0 ml per 100×15 mm plate); (2) bi-plates containing plain HSTB agar in one half of the plate (e.g., 10.0 ml) and selective HSTB agar in the second half; and (3) bi- or multi-segment plates containing plain HSTB agar in one segment and HSTB agar containing a suitable amount of a drug to be tested in each of the other segments (i.e., with each different drug or each different concentration of the same drug being contained within a separate segment).

Examples of Suitable Plate Designs

Examples of plates that are particularly useful for testing drug susceptibility/resistance of *M. tuberculosis* include, but are not limited to:

(1) Bi-plates for susceptibility testing with PZA, or any other drug as discussed previously herein, with side 1 of the plate containing HSTB agar with a suitable concentration of PZA (e.g., 1200 μg/ml), and side 2 containing the drug-free HSTB agar as control.

(2) Multi-Plate A—a four-segment plate for direct drug susceptibility test with two drugs only (INH and RMP). It is advisable to use it along with a bi-plate containing plain and selective HSTB agar. The distribution of the segments or wells in the drug-containing plates is as follows: 1—Drug-free control; 2—INH 0.2 μg/ml; 3—INH 1.0 μg/ml; and 4—RMP 1.0 μg/ml.

(3) Multi-Plate B—a six-well plate for indirect susceptibility testing with four drugs (INH, RMP, SM, and PZA). The distribution of the segments or wells in the drug-containing plates is as follows: 1—Drug-free control; 2—INH 0.2 μg/ml; 3—INH 1.0 μg/ml; 4—RMP 1.0 μg/ml; 5—SM 8.0 μg/ml; 6—PZA 1200 μg/ml.

(4) Multi-Plate C—a six-well plate for an indirect test with five more drugs (EMB, ETA, AK or KM, CM, Levofloxacin). The distribution of the segments or wells in the drug-containing plates is as follows: 1—Drug-free control; 2—EMB 14 μg/ml; 3—ETA 14 μg/ml; 4—AK (KM) 6.0 μg/ml; 5—CM 10.0 μg/ml; 6—Levofloxacin 4.0 μg/ml.

(5) Multi-Plate D—a four-segment plate for an indirect susceptibility test with three reserve drugs (PAS, cycloserine, clofazimine). The distribution of the segments or wells in the drug-containing plates is as follows: 1—Drug-free control; 2—PAS 8.0 μg/ml; 3—Cycloserine 60.0 μg/ml; 4—Clofazimine 6.0 μg/ml.

Protocol for Preparation of HSTB Agar

List of Supplies and Working Stocks:

Standard Laboratory Equipment:

Biosafety cabinet for sterile work (class I or II)

Autoclave

Regular incubator, set at 35–37° C.

Refrigerator and containers or brown paper bags to protect the plates from light Analytical balance Waterbath set at 54–56° C.

Vortex

70° C. freezer

Magnetic stir plate

Supplies (Example Source):

Sterile four-segment plastic plates (Fisher)

Sterile plastic 6-well tissue culture plates (Life Sci. Prod.)

Plastic zip-lock bags (sandwich bags)

Sterile Erlenmeyer flasks with frosted mouth, 500 ml or 1000 ml

Sterile pipets, 1 ml, 5 ml, 10 ml, 25 ml

Pipetting device

Middlebrook and Cohn 7H10 agar base powder (Fisher)

Calf serum filter sterilized (Sigma)

Glycerol $KH_2PO_4$ (Fisher)

Weighing dishes (Fisher)

Weighing spatula

De-ionized water

Sterile water for irrigation (Abbott)

15 ml conical tubes (Fisher)

Graduated cylinder, 100 ml

Volumetric flasks, 25 ml and 50 ml

Magnetic stir bars

Antimicrobial Agents for Selective Medium

PACT: drugs used in the selective agar (if bi-plates are prepared for culture isolation to be used along with plates of type A):

Polymixin B (Sigma, A3800406-001)

Add 5.0 ml of sterile distilled water to 50 mg to obtain 100,000 units per ml. Dispense in 1.0-ml amounts and store at −70° C.

Carbenicillin (Geopen) (Sigma, C1389)

Add 50 ml of sterile distilled water to 5 g to obtain a solution containing 100,000 μg/ml. Dispense in 1.0-ml amounts and store at −70° C.

Amphotericin B (Fungizone) (Sigma, A4888)

Add sterile distilled water to a vial containing the drug to obtain a solution of 10,000 μg/ml. Dispense in 1.0-ml amounts and store at −70° C. This drug is light sensitive. Keep vials wrapped in foil.

Trimethoprim Lactate (Sigma, T7883)

Activity is 1000 μg/ml. Prepare an aqueous solution containing 10,000 μg/ml. Filter sterilize and store at −70° C.

Preparation of Drugs for Susceptibility Testing (Example Source)

Drugs must be chemically pure, not from the pharmacy stock. When ordering drugs, one should get information regarding the biological activity in micrograms activity per milligram weight. If the biological activity is not 100% of the dry weight, the following approach is used to prepare the stock solution. To determine the needed powder weight, multiply the desired drug concentration (μg/ml) by the desired volume of the solution to be made (ml), and divide by the drug potency (mg per gram). For example, to make 25 ml of a solution containing 10,000 μg/ml of a drug with 800 mg per gram potency: [10,000×25]: 800=312.5 mg.

This amount of the drug powder should be weighed on a well calibrated analytical balance, and fully dissolved in 25 ml of appropriate solvent, using volumetric class A flasks.

Stock drug solutions of the water-soluble TB agents (all except RMP) are made with sterile or non-sterile water but must be filter-sterilized in either instance using a membrane filter with a pore size of 0.22 μm. Subsequent dilutions are made in sterile water for irrigation. Stock solutions should be made at concentrations of 1000 μg/ml to 10,000 μg/ml, as shown below, in a volumetric flask and stored in sterile freezer vials at −70° C. for up to 6 months. After thawing, the drug must be used immediately. The drug solution should never be re-frozen.

Most of the pure drug powders listed below are also available from US Pharmacopean Convention, Inc., Reference Standards, Order Department, 12601 Twinbrook Parkway, Rockwille, Md 20852.

Isoniazid (INH, Sigma)

Usual activity is 1000 μg/mg. Prepare an aqueous solution containing 2,000 μg/ml and filter sterilize. Dilute in sterile water to 20 μg/ml and 4 μg/ml for the working solutions.

Streptomycin Sulfate or Di-hydro-streptomycin (SM, Sigma, S6501)

Usual activity is 780 μg/mg. Prepare an aqueous solution containing 8,000 μg/ml and filter sterilize. Dilute in sterile water to 160 μg/ml for the working solution.

Rifampin (RMP, Sigma)

Activity is 1000 μg/mg. Prepare a solution containing 2,000 μg/ml in methanol or in 95% ethanol. This is a self-sterilizing solution. Dilute to 20 μg/ml in sterile water for the working solution.

Pyrazinamide (PZA, Sigma)

Usual activity is 1000 μg/mg. Prepare an aqueous solution containing 12,000 μg/ml. Filter sterilize. This is the working solution.

Ethambutol (EMB, Sigma)

Usual activity is 1000 μg/mg. Dissolve 200 mg in 20 ml of distilled water to have a solution of 10,000 μg/ml. Filter sterilize.

Etionamide (ETA, Sigma)

Usual activity is 10,000 μg/mg. Dissolve 100 mg in 20.0 ml of ethylene glycol (analytical grade) or 250 mg in 50.0 ml to obtain a stock solution containing 5,000 μg/ml. Incubate overnight at 37° C. for self-sterilization. Heat gently if not completely dissolved. Aliquots (1.5 ml) should be kept at −20° for not more than 3 months.

Capreomycin Sulfate (CM, Sigma)

Activity varies with each lot. Taking into account the actual activity, prepare an aqueous solution containing 10,000 μg/ml. Filter sterilize, and keep the aliquots for not more than 2 months at −20° C.

Amikacin (AK, Sigma, Free Base) or Kanamycin Sulfate (KM, Sigma)

Activity is varied. Prepare aqueous solution containing 10,000 μg/ml of the active product, filter sterilize, and keep the frozen aliquots for not more than 6 months.

Levofloxacin (from RW Johnson or Ortho-McNeil)

Activity is 1,000 μg/mg. Prepare aqueous solution of 80.0 μg/ml, filter sterilize. This is a working solution.

p-aminosalicylic acid (PAS, Sigma)

Prepare a solution of 8,000 μg/ml taking into account the actual potency of the batch.

D-Cycloserine (CS, Sigma)

Usual activity is 1,000 μg/mg, but in case of DL-Cycloserine the usual activity is 500 μg/mg. Prepare 6,000 μg/ml solution in a $Na_2CO_3$ solution that has pH 10.0. The later is prepared by using 0.1% solution of $Na_2CO_3$ to be added to 100 ml of distilled water until pH reaches 10.0. Frozen aliquots should be kept for not more than one month.

Clofazimine (CF,Sigma)

Usual activity is 1,000 μg/mg. A 100 μg/ml solution should be made in DMSO. Subsequent dilutions are made also in DMSO. The aliquots can be kept for not more than one month at room temperature, protected from light.

Protocol for Production of Plain HSTB Agar for Any of the Drug-free Controls, for a Bi-plate, or for a Whole Plate:

The optimal volume that is easy to handle in the clinical laboratory is 200 ml or 300 ml agar per 500 -ml or 1000 -ml flask, although the volumes can be adjusted, as can be readily determined by one of skill in the art. Calculations for drug-containing media are given here for 200 ml of the medium to prepare 40 drug-plates, based on approximately 5 ml of agar per well or segment. One of skill in the art will be able to modify the calculations to accommodate different volumes of medium. In addition, one of skill in the art will be able to modify the percentage of animal serum, or modify the pH, within the ranges set forth previously herein, as desired. The following recipes are designed to produce an HSTB medium containing about 10% animal serum and to be at a pH of from about 6.0 to about 6.25.

Plain HSTB Agar

In a 500 ml Erlenmeyer flask add the following:

Magnetic stir bar 3.6 g 7H10 agar base 1.2 g $KH_2PO_4$ 180 ml de-ionized water 1 ml glycerol Autoclave at 121° C. for 10–12 min.

Cool in waterbath to 54–56° C.

Add 20 ml of sterile calf bovine serum (CBS), or other suitable animal serum as described previously herein, warmed to room temperature. Stir ingredients using a magnetic stir bar on a magnetic stir plate being careful not to create bubbles. Pour approximately 5 ml of agar into the segments or wells by tilting the flask, or use a pipet. Always use aseptic technique in all media preparation procedures. Allow the plates to completely cool and solidify. Store plates in plastic bags (to keep from drying out) away from light at 4–5° C.

If the bi-plate for culture isolation is prepared, the procedure is the same, but 10 ml is used per each half of the plate.

Selective Agar

This medium is intended for the bi-plates if they are used along with plates of type A (or other plates designed for direct drug susceptibility testing). Preparation of the medium is the same as for the plain agar (see above), but along with the serum, four drugs (PACT) are added to have the final concentrations shown below. About 10 ml of this medium is used in the second half of the bi-plate.

| | |
|---|---|
| Polymyxin B* | 200 units/ml (25 μg/ml) |
| Amphotericin B | 10 μg/ml |
| Carbenicillin | 50 μg/ml |
| Trimethoprim | 20 μg/ml |

*1 unit polymyxin B sulfate = 0.127 μg

Agar with INH Low Concentration

Follow the directions for the plain agar except reduce the water to 170 ml. After the agar has cooled to 54–56° C. add 20 ml of serum and 10 ml of the INH working solution (4.0 μg/ml) for a final concentration of 0.2 μg/ml.

Agar with INH High Concentration

Follow the directions for the plain agar except reduce the water to 170 ml. After the agar has cooled to 54–56° C. add 20 ml of serum and 10 ml of the INH working solution (20 μg/ml) for a final concentration of 1.0 μg/ml.

Agar with RMP

Follow the directions for the plain agar except reduce the water to 170 ml. After the agar has cooled to 54–56° C. add 20 ml of serum and 10 ml of the RMP working solution (20 μg/ml) for a final concentration of 1.0 μg/ml.

Agar with SM

Follow the directions for the plain agar except reduce the water to 170 ml. After the agar has cooled to 54–56° C. add 20 ml of serum and 10 ml of the SM working solution (160 μg/ml) for a final concentration of 8.0 μg/ml.

Agar with PZA

Follow the directions for the plain agar except reduce the water to 160 ml. After the agar has cooled to 54–56° C. add 20 ml of serum and 20 ml of the PZA working solution (12,000 μg/ml) for a final concentration of 1200 μg/ml. Since this concentration is closed to the saturation point, the thawed solution must be inspected for crystals before using. Vortex and incubate for 10–15 minutes at 37° C. if crystals are present.

Agar with EMB

Prepare a working solution by diluting the stock solution 1:40 in distilled water. Prepare the agar in 170 ml, and add, after cooling, 20 ml of serum and 10 ml of the working drug solution (280 μg/ml) to have the final drug-concentration of 14 μg/ml.

Agar with ETA

Follow the same instruction as for EMB.

Agar with AK(KM)

Prepare a working solution by diluting 1:100 the stock solution in water. Prepare agar in 168 ml, and add, after cooling, 20 ml of serum and 12 ml of the working drug solution (100 μg/ml) to have the final drug-concentration of 6.0 μg/ml.

Agar with CM

Prepare a working solution by diluting 1:100 the stock solution. Add to 160 ml of the cooled agar 20 ml of serum and 20 ml of the drug working solution (100 μg/ml) to have the final drug-concentration of 10.0 μg/ml.

Agar with Levofloxacin

Add 20 ml of serum and 10 ml of the stored (see above) drug working solution (80 μg/ml) to 170 ml of cooled agar to have the final drug-concentration of 4.0 μg/ml.

Agar with PAS.

Prepare a working solution by diluting 1:100 the stock. Add 20 ml of serum and 20 ml of the working solution (80 μg/ml) to 160 ml of cooled agar to have the final drug-concentration of 8.0 μg/ml.

Agar with CS.

Prepare a working solution by diluting the stock 1:10. Add 20 ml of serum and 20 ml of the working solution (60 μg/ml) to 160 ml of cooled agar to have the final drug-concentration of 6.0 μg/ml.

Agar with CF.

To 168 ml of cooled agar add 20 ml of serum and 12 ml of the working solution (100 μg/ml in DMSO—see above) to have the final drug-concentration of 6.0 μg/ml.

Composition of the Plates

The optimal is 40 plates per batch, although it is well within the ability of those of skill in the art to vary the batch according to preference. For example, six flasks of medium are needed for preparation of the six-well plates of type B or C, or four flasks for four-segment plates of type A, at 200 ml each. The flasks should be made simultaneously for such a batch. Each plate is labeled with the batch number or date of preparation and placed in an individual plastic bag. Each batch is stored in a container to be protected from light and kept refrigerated until use.

Quality Control

A pre-characterized susceptible *M. tuberculosis* isolate should be used to ensure the potency of the drugs incorporated into the agar. This quality control strain should be inoculated onto the plates every time a batch of clinical isolates is tested. Plates should not be used until proven appropriate in a test with the QC strain.

General Directions for Plate Preparation, Storage and Use

The drugs are incorporated into the medium in tentative critical concentrations such as those described above for the exemplary plates, but it is to be understood that these concentrations can be validated or altered subsequent to further study. INH is included in two concentrations with the intention of detecting two types of INH-resistance (low and high). Each plate is enclosed in a plastic zip-lock bag, and should be kept refrigerated until use. The tentative shelf-life is three months from the date of preparation, which may be extended after proper evaluation. The plates should be kept out of light during storage and the subsequent use.

The plates should be removed from the refrigerator a few hours before intended use, and placed at room temperature on the bench, in plastic bags, covered. The plates should be removed from the plastic bags prior to inoculation under the hood (biosafety cabinet), and labeled appropriately. After inoculation, the plates should remain under the hood until the inoculum is well absorbed by the medium. Sometimes, it is necessary to place the lid slightly off the plate to facilitate this drying process. After the plates have dried, place them inside the plastic zip-lock bags, seal individually, and only after that remove them from the hood.

General Protocol for Drug Susceptibility Testing Using HSTB Agar Medium

The novel agar medium of the present invention (HSTB) is designed for cultivation of *M. tuberculosis* in regular incubators, without supplemental $C0_2$ in the atmosphere. By way of example, the following protocols describe the use of plates of type A, B and C, as discussed above.

Culture Isolation and Direct Drug Susceptibility Test Using Type A Plates:

The type A plate should be used for culture isolation and direct susceptibility testing for smear-positive specimens only. Sputum specimens should be processed by the NaOH-NALC method with pH neutralization using a proper concentration procedure (see below). At least one more unit of culture medium, an L-J slant, or better, an agar bi-plate (with plain and selective HSTB agar), should be used for culture isolation. In addition, inclusion of a liquid medium, for example a Bactec vial, a MGIT tube, or a Redox tube, etc, may shorten the turnaround time of the laboratory report and increase the overall rates of culture recovery. All these culture media should be inoculated with an undiluted specimen. At the same time, to obtain valid results of the direct drug susceptibility test, the inoculum for plate A should be diluted, if necessary, based on the smear-examination results:

1) specimen showing ≦25 AFB/field (1+)—inoculate 0.1 ml of the undiluted specimen per segment, or 0.2 ml if there is only <5 AFB/field;
2) specimen with 25–50 AFB/field (2+)—inoculate one plate with 0.1 ml of the undiluted specimen per segment and the other with 0.1 ml of a 1/10 dilution ($10^{-1}$);
3) specimen with 50–250 AFB/field (3+)—use undiluted specimen and $10^{-2}$ dilution;
4) specimen with >250 AFB/field (4+)—use 10–2 and $10^{-4}$ dilutions.

Indirect Drug Susceptibility Test Using Plates Type B, C or D

A bacterial suspension from colonies homogenized in a tube containing 7H9 broth and glass beads, or a culture grown in any of the liquid media, is adjusted to the optical density of a McFarland No. 1 standard. Two dilutions are made at $10^{-2}$ and $10^{-4}$ in saline or 7H9 broth, inoculated in the amount of 0.1 ml per well, using two plates per culture. If a culture is obtained from a BACTEC vial with daily GI 999, dilute $10^{-1}$ and $10^{-3}$ and inoculate 0.1 ml each per well. The covered plates are tilted to spread the inoculum avoiding the edges as much as possible and left under the hood for at least one hour until the liquid has fully absorbed into the agar.

Incubation for All Plate Types

The bagged plates are removed from the safety cabinet, stacked no more than six plates high, agar side down, in wire baskets, and incubated in regular incubators at 35–37° C. for 21 days, protected from light. After incubation, upon removal from the incubator, the plates should be turned up side down (agar up), and left in bags overnight at room temperature to eliminate condensation. Some strains may not produce visible growth after 3 weeks of incubation. If the culture has not grown yet, the plates should be re-incubated for additional 3 weeks, but there is a limit for interpretation of the drug susceptibility test results if the culture had to be incubated for 6 weeks (see below).

Counting of the colonies and interpretation

The results of the drug susceptibility test are considered valid if the results with the QC strain(s) are in agreement with the established laboratory standards, and if the number of colonies grown in drug-free wells are no less than 50, but, even better, greater than 100. This number should not be greater than 300, especially for interpretation of "resistant" results. The colonies are examined for purity and counted under a dissecting microscope without removing the plate from the plastic bag. The results are reported as a percentage of resistance. For this purpose, the number of colonies in a drug-containing well or segment is divided by the number of colonies grown on the drug-free control and multiplied by 100. If the percentage is greater than or equal to one, the culture is considered resistant to that drug concentration for INH, SM, and RMP. The breakpoint for PZA is 10%. If growth is present on the drug-containing media, the colonies must be counted. Over-inoculation may result in a false resistant interpretation. The standard procedure is applicable for cultures sufficiently grown after 3 weeks of incubation. For cultures not grown at 3 weeks and examined only after 6 weeks of incubation, the results of the drug susceptibility test are reportable only if the isolate shows no drug resistance (no growth on the drug-containing medium).

The records during the period of evaluation of new agar plates should include the following information: source of the inoculum (medium), its actual preparation, number of colonies grown in each well, and the interpretation. It is desirable that the laboratory's conventional susceptibility method is performed along with the use of the new agar plates.

Biosafety

Specimen and/or culture handling including all procedural steps up to the incubation step or removal of the plate from the plastic bag should be performed in a Class 2 Biological Safety Cabinet in a Biosafety Level 3 facility. Use extra care with pipets or pipetting devices that can result in high-pressure inoculation as the inoculum can splatter off the agar medium and create an aerosol. Examination of the plates in an open bench area of the laboratory should be done without opening the plastic bags, as described above. Special attention should be given to elimination of the condensation by placing the plates after incubation and before examination in an upside down (agar up) position overnight at room temperature. Removal of the plates from the plastic bags can be considered for the purpose of culture isolation from colonies grown on drug-free segments only. This work should be done in the biosafety level 3 facility with all appropriate precautions. Cultures on agar plates should never be shipped through the mail due the possibility of the agar shaking loose of the plate.

Preparation of Samples for Drug Susceptibility Testing

NaOH-NALC Digestion-Decontamination Procedure with Neutralization

Rationale.

The problem faced in the laboratory is one of balancing the need for a gentle decontamination procedure that maintains viability of the mycobacteria with the need to eliminate all other organisms. None of the decontamination techniques available meets this criterion perfectly. It should be realized that even under the best of conditions only 10–20% of mycobacteria found in a clinical specimen survive the decontamination process. The procedure outlined below (NaOH-NALC method with neutralization) exploits the relative resistance of acid-fast bacteria to the effects of alkali and/or acids in order to separate them from other microorganisms. The mucolytic agent N-acetyl-L-cysteine (NALC) is used for digestion of mucus to homogenize the sputum. Sodium hydroxide (NaOH) is used to eliminate contaminating microorganisms, while leaving an adequate number of viable mycobacteria. After decontamination, a phosphate buffer solution and a solution of hydrochloric acid (HCl) should be used to neutralize the NaOH. Only this technique is suitable for inoculation of the agar, particularly for a direct drug susceptibility test on HSTB agar plates of type A.

Solutions Required

NaOH-NALC Solution ("digestant" solution)

Sodium hydroxide stock solution: dissolve 200 ml of NaOH solution (50% w/w) in 1000 ml distilled water.

Sodium citrate stock solution: dissolve 147 g of Sodium Citrate ($Na_3C_6H_507.2H_20$) in 1000 ml distilled water.

Working solution: mix together the two solutions above and add distilled water to make a final volume of 5000 ml. Store in brown plastic bottles, 250 or 500 ml in each, at 2–8° C., for not more than 2 months.

Final digestant: Just before use, add 0.5 g of N-acetyl-L-cysteine powder (NALC) to every 100 ml of the working solution. Prepare only the volume of final digestant needed for one day, because the mucolytic activity of NALC is lost upon standing. The final digestant must be used within 18–24 hours. The composition of the final digestant solution is:

2% (0.5 M) NaOH 0.1 M Sodium Citrate 0.5% NALC.

To avoid a possibility of cross-contamination, never pour the digestant solution (as well as other reagents) to the tubes containing specimens directly from the flask. Instead, make aliquots of this solution first, in volumes corresponding to the volumes of the specimens (8.0 ml each for this study), label with the volume and specimens' numbers, and place them against the corresponding specimens. Pour aliquots into corresponding specimens.

Phosphate Buffer Solution

To make a 0.5 M phosphate buffer solution with pH 6.0, dissolve in 1000 ml distilled water:

8.7 g $Na_2HPO_4$ (dibasic sodium phosphate)

59.7 g $KH_2PO_4$ (monobasic potassium phosphate)

40 mg Phenol Red Sodium Salt

Note: these figures are for anhydrous chemicals. If phosphates are hydrated, values must be adjusted accordingly.

If necessary, the solution may be warmed slightly to facilitate dissolving of the salts. Sterilize buffer by autoclaving for 15 min, label and store at 2–8° C. Aliquot buffer for each specimen, using another 50 ml centrifuge tube, then pour into each specimen rather than pouring from a common flask. Make in advance aliquots, 16 ml each. Keep them refrigerated.

Hydrochloric Acid

Hydrochloric acid (HCl), at a concentration of 0.5 M, will be needed for neutralization of the processed specimens that have alkaline pH because of treatment with NaOH. The concentration of bulk "concentrated" HCl varies from about 36.5–38%. A 37% solution of HCl is equivalent to 11.9 M. To make 1000 ml of a 0.5 M HCl solution from 37% solution, first place about 800–900 ml of distilled water into a volumetric flask. Then add 42 ml of 37% solution, mix, and bring the total volume up to 1000 ml. When working with concentrated acids, for safety's sake, always add the acid to a larger volume of water. NEVER add water to concentrated acids because the generated heat can cause the acid to splash or explode. Make aliquots, 8.0 ml each, and keep them refrigerated.

20% Animal Serum Solution

Prepare a solution by adding 20 ml of sterile animal serum to 80 ml of sterile distilled water, filter sterilize, and make 2.0-ml aliquots to be kept refrigerated. Two ml of this solution will be used to re-suspend each pellet of bacteria after the decontamination procedure.

Procedure for Sputum Specimens Processing

1. Sputum specimens are usually collected in sterile 50-ml plastic screw-cap centrifuge tubes. Specimens collected otherwise should be transferred into such 50-ml tubes. Place 8 ml of sputum specimen into a sterile 50-ml tube. If the submitted specimen contains more than 8 ml of sputum, the specimen should be distributed among 2 or 3 tubes. If the volume of the submitted specimen is less than 8 ml, add, using individual pipettes for each specimen, sterile saline to bring the volume up to 8 ml. Add 8 ml of the described above digestant solution from the prepared aliquots to the specimen. The total volume of the specimen is now 16 ml, and the concentration of NaOH in the sputum/digestant mixture is 1%, or 0.25 M. Stopper tightly and mix for approximately 20 seconds on a vortex mixer. Do not swirl contents up into the cap or shake by hand after vortexing.
2. Allow the mixture to stand for exactly 15 minutes at room temperature.
3. Add 16 ml of 0.5M phosphate buffer to the sputum/digestant mixture. Stopper tightly and mix carefully.
4. Add 8 ml of 0.5M hydrochloric acid solution to the specimen. Stopper tightly and mix carefully. The pH of the specimen should now be 7.0 or less, and the color of the specimen should now have a yellow color.
5. Centrifuge at 3500×g for at least 25 minutes in a refrigerated centrifuge that has aerosol-containment buckets.
6. Cautiously, avoiding disturbance of the pellet, decant supernatant fluid into a canister/funnel arrangement containing 5% amphyl solution.
7. Prepare smears by dipping a wooden applicator stick into the concentrate and drawing it across the surface of the slide. Allow slides to dry under the hood. Place on a slide warmer to heat-fix at 68° C. for 2 hours.
8. Stain slides, examine, and report results accordingly.
9. Add 2.0 ml of sterile animal serum solution to the pellet.
10. Inoculate various media for culture isolation with the undiluted concentrated specimen, and prepare dilutions for the direct susceptibility test on the plate A according to smear results.

The following examples are provided for the purpose of illustration and are not intended to limit the scope of the present invention.

EXAMPLES

Example 1

The following example describes cultivation of *Mycobacterium tuberculosis* on HSTB agar medium without $CO_2$.

HSTB agar.

The commercially available Middlebrook/Cohn 7H10 agar base (BBL, Becton Dickinson and Co., Cockeysville, Md.) was dissolved in deionized water, 3.6 g of the powder per 160 ml of distilled water, in 500-ml Erlenmeyer flasks containing magnetic stir bars. Then 1.2 g of monopotassium phosphate ($KH_2PO_4$) to acidify the medium and 1.0 ml of glycerol was added per flask. After being autoclaved at 121° C. for 12 min., the flasks were placed into the water bath to cool down to 54° C. The standard animal serum product to be added to the agar was obtained from Sigma Chemical Co. The serum used was fetal bovine serum (FBS), calf bovine serum (CBS), or fetal equine serum (FES). Preliminary studies indicated that any type of serum from these sources equally supported growth of *M. tuberculosis* strains. Most of the results presented this and subsequent examples were performed with HSTB agar containing CBS in the amount of 10% to the final volume of the agar medium. The most convenient way to prepare the agar in the clinical laboratory setting is by making 200-ml portions of the medium. For this purpose, flasks with agar cooled to 54° C., and 160 ml in each were placed as described above on the magnetic plate for subsequent mixture with the added serum. Each 160-ml portion was supplemented with 40 ml of a separately prepared mixture of 20 ml of serum (warmed up to the room temperature) plus 20 ml of a drug solution (See Examples 3–4), or 20 ml of distilled water for a drug-free medium (this Example), so that the final volume in each flask was 200 ml, and the final pH of the medium was 6.15±0.1. The same batches of agar were used in parallel to prepare standard 7H10 and 7H 1 agar containing OADC for comparison with the HSTB agar.

Results.

A total of 60 *M. tuberculosis* cultures were tested by incubation at 37° C. without supplemental $CO_2$, as well as in the presence of 5–7% of $CO_2$ in the atmosphere. Growth of all strains was recovered on HSTB agar with or without $CO_2$ within three weeks of cultivation. Only 52 of these strains were also tested for growth on 7H10 and 7H11 agar plates. Four of these 52 strains did not grow on these media without $CO_2$. The present inventors' have previously determined that generally, about 20% of *M. tuberculosis* isolates will not grow on 7H10/7H11 agar without 5–7% of $C0_2$ in the atmosphere. The morphology of the colonies on HSTB agar was slightly different from that on 7H10/7H11 agar: the colonies were smaller, more domed, and less spread on the surface of the medium.

Example 2

The following example describes the comparison of ADC, OADC, and animal serum as supplements in 7H10/7H11 agar media.

It was previously speculated that oleic acid may inhibit the bacterial growth at low pHs, and therefore it was suggested to use ADC instead of OADC for 7H10/7H11 agar media to obviate the growth inhibition at the acidic pH of 5.5 (Butler et al., *J. Clin. Microbiol.,* 16:1106–1109, 1982; Butler et al., *Antimicrob Agents Chemother.,* 24:600–601, 1983). In an attempt to create optimal conditions for *M. tuberculosis* growth at the acidic pH, the present inventors compared growth of three strains (H37Rv, Erdman and Atencio) on 7H11 agar supplemented with 10% of OADS vs ADS vs equine fetal serum (EFS) vs bovine fetal serum (BFS), all obtained from Sigma.

The commercially available Middlebrook 7H10 agar base (BBL, Becton Dickinson and Co., Lockeysville, Md.) was dissolved in deionized water, 14.4 g per 660 ml. Then 4.7–5 g of monopotassium phosphate ($KH_2PO_4$) was added to acidify the medium. In addition, 0.72 g of casein hydrolysate and 4.0 ml of glycerol were added. After autoclaving at 121° C. for 12 min, the medium was split into four sterile flasks, 160 ml per each. The flasks were placed into the water bath to cool down to 54° C. After that, 20 ml of the animal serum (bovine or equine fetal or calf serum from Sigma Chemical Co.) was added up to the total volume of 200 ml per flask. The final concentration of the serum was 10%, and the final pH was 6.15±0.1. For the purpose of comparison, similar media were made with OADC or ADC instead of the animal serum.

Two sets of whole plates (to have a duplicate) of the agar containing each of the supplements, one having standard pH 6.8 and one with pH 6.0, were inoculated simultaneously with 0.5 ml of the bacterial suspension, to have approximately 100 to 200 CFU per plate by using a 10–6 dilution of a bacterial suspension adjusted to the optical density of the McFarland Standard No. 1.

The results of experiments with three strains are shown in Table 1. These preliminary data showed that the recovery of *M. tuberculosis* an agar media supplemented with BFS was equal and sometimes even better than on the standard OADC-containing medium at pH 6.0, and no worse than on the media with pH 6.8. At the same time, growth at pH 6.0 on the media supplemented with ADC was partially suppressed compared with the media with either OADC or BFS. In addition, we should stress that the size and appearance of colonies at the three-weeks reading on the Ph 6.0 medium with BFS was no different from that with pH 6.8.

TABLE 1

Number of CFU grown on four types of agar medium, each at pH 6.8 and 6.0. Two counts separated by a slash represent the numbers on two plates

| | pH 6.8 | | | pH 6.0 | | |
|---|---|---|---|---|---|---|
| Supplement | H37Rv | Erdman | Atencio | H37Rv | Erdman | Atencio |
| OADC | 56/32 | — | 70/29 | 72/71 | 29/13 | 76/77 |
| OADC | 50/63 | 77/68 | 82/102 | — | — | — |
| ADC | 45/31 | 73/60 | 100/101 | 5/6 | 3/9 | 39/72 |
| EFS | 55/68 | 57/91 | 96/92 | 57/66 | 52/41 | 0/0 |
| BFS | 50/63 | 64/72 | 55/13 | 65/62 | 60/66 | 84/94 |

Example 3

The following example describes the determination of the INH and RMP critical concentrations for use in HSTB agar medium.

The purpose of this study was to determine the highest MICs of the tuberculosis drugs, isoniazid (INH) and rifampin (RMP) for pansusceptible strains, and the lowest MICs for INH- and RMP-resistant clinical isolates, using HSTB and 7H11 agar medium in parallel. A broad range of concentrations of either INH or RMP was incorporated into HSTB and 7H11 agar media.

Preparation of the Four-segment Plates with Two Drugs.

Four-segment plastic plates, 100×15 mm, were used to have plain agar (segment I), agar with 0.1 μg/ml and 1.0 μg/ml of isoniazid (segments II and III), and agar with 2.0 μg/ml of rifampin (segment IV), plated at about 5.0 ml of the medium per segment. The HSTB agar was prepared as described in Example 1. Stock solutions of isoniazid (INH) were made in distilled water (filter-sterilized), and the stock solution of rifampin (RMP) was made in methanol. Aliquots of the stock-solutions were preserved at −70° C. To make an agar containing 0.1 μg/ml of INH, 20 ml of the INH working solution containing 2.0 μg/ml of the drug was mixed with 20 ml of serum, and added to 160 ml of agar cooled to 54° C. To prepare the medium containing 1.0 μg/ml of INH, 20 ml of the working drug solution containing 10 μg/ml was mixed with 20 ml of serum, and added to 160 ml of agar cooled to 54° C. For the RMP-containing agar, 20 ml of the working aqueous solution containing 20 μg/ml of this drug was mixed with 20 ml of serum, and added to 160 ml of agar, resulting in the final concentration of 2.0 μg/ml of RMP.

Results.

The MICs of INH for 13 *M. tuberculosis* pan-susceptible strains were as follows. On 7H11 agar: MIC of 0.05 μg/ml was found for eight strains, and MIC of 0.2 μg/ml was found for five strains. On HSTB agar, MIC of INH was 0.2 μg/ml for all 13 strains. These data indicated that the highest MICs of INH for both types of agar were the same, 0.2 μg/ml. The MICs of INH for ten strains previously identified as INH-resistant were as follows: eight strains on HSTB and seven strains on 7H11 agar had an MIC greater than 3.2 μg/ml, MIC of 1.6 μg/ml was found for one strain on both media, MIC of 0.8 μg/ml also was found for one strain on 7H11 agar only. The conclusion from these data is that the activity of NH on HSTB was not significantly different from that on 7H11 agar. These data justify the same critical concentration on both media: 0.2 μg/ml for detection of the low level, and 1.0 μg/ml for detection of the high level of resistance to INH.

The MICs of RMP for 13 susceptible strains were as follows: on 7H 11 agar within the range (μg/ml) of 0.03 (1 strain)—0.125 (9 strains)—0.5 (3 strains); on HSTB agar (μg/ml)—0.125 (3 strains)—0.5 (9 strains)—1.0 (1 strain). These data suggest that the MICs of RMP were higher on HSTB agar than on 7H11 agar, with one strain having 1.0 μg/ml. Results of testing 11 RMP-resistant strains were the same on both media: MIC of one strain was 4.0 μg/ml, and MICs of 10 strains were greater than 16.0 μg/ml. These data suggest that the critical concentration of RMP on HSTB agar should be 2.0 μg/ml rather than 1.0 μg/ml adopted for 7H11 agar.

TABLE 2

MICs (mcg/ml) of INH for 13 Susceptible Strains on Agar Media

| 7H11 | HSTB 0.05 | 0.2 | Total |
|---|---|---|---|
| 0.05 | 0 | 8 | 8 |
| 0.2 | 0 | 5 | 5 |
| Total | 0 | 13 | 13 |

MICs (mcg/ml) of INH for 10 Resistant Strains on Agar Media

| 7H11 | HSTB 0.4 | 0.8 | 1.6 | ≧3.2 | Total |
|---|---|---|---|---|---|
| 0.4 | 0 | 0 | 1 | 0 | 1 |
| 0.8 | 0 | 1 | 0 | 0 | 1 |
| 1.6 | 0 | 0 | 0 | 1 | 1 |
| ≧3.2 | 0 | 0 | 0 | 7 | 7 |
| total | 0 | 1 | 1 | 8 | 10 |

TABLE 3

MICs (mcg/ml) of RMP for 13 Susceptible Strains on Agar Media

| 7H11 | HSTB 0.03 | 0.12 | 0.5 | 1.0 | Total |
|---|---|---|---|---|---|
| 0.03 | 0 | 1 | 0 | 0 | 1 |
| 0.12 | 0 | 2 | 7 | 0 | 9 |
| 0.5 | 0 | 0 | 2 | 1 | 3 |
| 1.0 | 0 | 0 | 0 | 0 | 0 |
| TOTAL | 0 | 3 | 9 | 1 | 13 |

MICs (mcg/ml) of RMP for 11 Resistant Strains on Agar Media

| 7H11 | HSTB 4.0 | ≧16.0 | Total |
|---|---|---|---|
| 4.0 | 1 | 0 | 1 |
| ≧16.0 | 0 | 10 | 10 |
| Total | 1 | 10 | 11 |

Example 4

The following example describes the isolation of *M. tuberculosis* from sputum on HSTB plates.

Preparation of the Agar Bi-plates.

Plastic bi-plates, 100×15 mm, were used for having plain (I) and selective (II) HSTB agar. Four drugs under the PACT acronym, the same as for the 7H10/7H11 agar, were used to make the medium selective. Stock solutions of each of these drugs were prepared in advance. Polymyxin B (Sigma, A3800406-001) was kept in an aqueous solution of 100,000 units per ml (unit=0.127 μg). Amphotericin B (Fungizone, Sigma, A4888) was kept protected from light in an aqueous solution containing 10,000 μg/ml. Carbenicillin (Geopen, Sigma C1389) was also kept in an aqueous solution containing 100,000 μg/ml. Trimethoprim Lactate (Sigma, T7883) was prepared in a 10,000 μg/ml aqueous solution.

The drug solutions were kept at −70° C. in 1.0-ml aliquots, and after thawing, a mixture (PACT) was prepared in the following manner:

| | |
|---|---|
| Polymyxin B | 0.5 ml |
| Amphotericin B | 0.5 ml |
| Carbenicillin | 0.25 ml |
| Trimethoprim | 0.62 ml |
| Distilled water up to | 50.0 ml |

To make 200.0 ml of the selective agar medium, 20.0 ml of the PACT mixture combined with 20.0 ml of serum was added to 160.0 ml of the cooled agar and carefully stirred with magnetic bars to avoid bubbles. The final concentrations of drugs (μg/ml) in the selective agar medium were: P—200 units, A—10 μg, C—50 μg, T—20 μg. Each half of the bi-plate contained about 10.0 ml of either plain or selective agar. After solidification, each plate was placed in a separate zip-lock plastic bag and kept refrigerated, protected from light.

Inoculation and Cultivation.

Sputum specimens were processed by the standard NaOH-NALC procedure (described in the Detailed Description of the Invention), or by a 25 similar procedure with pH neutralization. The pellet obtained after concentration through centrifugation at 3500×g in an aerosol-contained refrigerated centrifuge should be diluted with bovine albumin or animal serum to have a sufficient volume to inoculate all necessary media. Bi-plates are inoculated with 0.2 ml of the concentrated specimen per each side of the plate, and 0.1 ml is needed per each segment of the four-segment plate. Each plate is left under the hood to allow the inoculum (spread by tilting of the plate) to be fully absorbed by the medium. Each plate is placed into a zip-lock bag. The plates, agar side down, are stacked no more than six plates high, in wire baskets, and incubated in regular incubators (without $CO_2$), protected from light. The plates are examined after three weeks of incubation, and in case of no growth or insufficient growth, also at four and six weeks. At any time-point, upon removal from the incubator the plates should be left in bags at the room temperature overnight, turned upside down (agar side up) to eliminate condensation. The colonies are examined and counted under dissecting microscope, without removing them from the plastic bags. If more detailed examination of the colonies is required, it should be done under the hood in the level 3 biosafety facility.

Results.

Twenty *M. tuberculosis* cultures were isolated from sputum specimens inoculated into five culture media: BACTEC 12B broth, MGIT broth, L-J slant, 7H11 agar (cultivation with $CO_2$), and HSTB agar (cultivation without $CO_2$). The best recovery rate was on HSTB agar (19 cultures), followed by BACTEC and MGIT broth (15 cultures each), 7H 11 agar (11 cultures), and L-J slant (9 cultures). Comparison of the results on two agar media indicated that two isolates did not grow on either medium, and seven cultures grew on HSTB, but not on 7H11 agar. Incorporation into the isolation protocol of the BACTEC liquid medium was important to supplement the results on 7H11 agar by adding six more positive cultures totaling in 17 positive results. This outcome was still less than 19 cultures on HSTB agar alone (95%).

Time to growth detection was shortest in the broth systems, MGIT and BACTEC: 12.1 and 14.2 mean number of days, with 50% and 30% reported within two weeks. The mean periods on 7H11 and HSTB agar were significantly longer (17.1 and 25.1 days) due to a few strains that required up to four to five weeks to produce visible growth. At the same time, 20% and 30% of the isolates were detected on these media within the first two weeks of cultivation.

These results show that HSTB agar was more efficient than 7H11 agar and all other media tested (L-J slant, BACTEC and MGIT broth) in recovery from the 20 sputum specimens evaluated. Incorporation of a liquid medium into isolation protocol increases the recovery rate and to shorten the turnaround time. With HSTB agar, the addition of a liquid medium is useful for shortening the time to detection of growth for a number of strains. At the same time, the recovery rate on HSTB agar was not less than in a combined use of 7H11 agar and BACTEC broth.

TABLE 4

Recovery of *M. tuberculosis* from Sputum Specimens on Different Media

| Smear Results (AFB/field) | No. of Isolates | No. of Positive Cultures on HSTB | 7H11 | L-J | BACTEC |
|---|---|---|---|---|---|
| 0 | 4 | 4 | 0 | 0 | 3 |
| <5 | 9 | 8 | 5 | 4 | 6 |
| ≧5 | 7 | 7 | 6 | 5 | 6 |
| TOTAL | 20 | 19 | 11 | 9 | 15 |

TABLE 5

Recovery of *M. tuberculosis* from 20 Culture-Positive Sputa: Combined Effect of 7H11 or HSTB Agar with 7H12 BACTEC Broth

| BACTEC | Pos. | Neg. | Total |
|---|---|---|---|
| | HSTB Agar | | |
| Pos. | 15 | 0 | 15 |
| Neg. | 4 | 1 | 5 |
| | 7H11 Agar | | |
| Pos. | 9 | 6 | 15 |
| Neg. | 2 | 3 | 5 |
| Total | 11 | 9 | 20 |

TABLE 6

Time to Recovery of *M. tuberculosis* from 20 Culture-Positive Sputum Specimens on Different Media

| Medium | No. of Positive | Days to Detection Mean | Range | % of Positive within 14 days |
|---|---|---|---|---|
| HSTB | 19 | 25.1 | 7–42 | 30.0 |
| 7H11 | 11 | 17.1 | 7–28 | 20.0 |

TABLE 6-continued

Time to Recovery of *M. tuberculosis* from 20 Culture-Positive Sputum Specimens on Different Media

| Medium | No. of Positive | Days to Detection Mean | Range | % of Positive within 14 days |
|---|---|---|---|---|
| Bactec | 15 | 14.2 | 3–28 | 30.0 |
| MGIT | 15 | 12.1 | 3–23 | 50.0 |

Example 5

The following example demonstrates that HSTB agar medium can be used with PZA to determine the actual proportion of PZA-resistant bacteria in a population. The example also demonstrates the use of HSTB agar medium in a PZA susceptibility test with clinical isolates.

The agar proportion method should provide the opportunity for determining the actual proportion of resistant bacteria in the population. To investigate the applicability of this option to PZA, the present inventors conducted experiments with artificially prepared mixtures containing various proportions of PZA-resistant bacteria. For this purpose, PZA-resistant mutants were developed by selection from two pansusceptible strains on agar plates containing 12 $\mu$g/ml. Mixtures with the original susceptible strains were prepared in a proportion of 10%, 25% and 50%, tested along with the original strains and the resistant mutants. All five cultures were tested by two methods: in the BACTEC PZA broth at 100, 300 and 900 $\mu$g/ml and on agar plates at 300, 900, and 1200 $\mu$g/ml.

Materials and Methods PZA was purchased from Sigma Chemical Co. (St. Louis, Mo.). The necessary solutions were made in distilled water. Three solutions were made to have the final concentrations of 300, 900 and 1200 $\mu$g/ml in the agar medium (see below).

The culture medium was prepared as described in Example 2. When the animal serum was added to the medium, 20 ml of the PZA-solution (or distilled water for the control) was also added up to the total volume of 200 ml per flask. The final concentration of the serum was 10%, and the final pH was 6.15±0.1.

The media were poured into the 100×15 mm four-segment petri dishes: No. 1—for the drug-free medium, and three remaining segments—for the agar containing three PZA concentrations. After completion of the quality controls for sterility and ability to support growth, the plates were stored at 4° C., protected from light, for a period not longer than eight weeks.

A culture of *M. tuberculosis* was subcultivated in 7H9 broth at 37° C. for a period of 4 to 7 days, and was adjusted using the same medium to the optical density of the McFarland Standard No. 1. Two dilutions of this suspension, $10^{-2}$ and $10^{-4}$, were used as an inoculum, 0.1 ml per segment, to inoculate two plates. The plates were sealed in individual polyethylene $CO_2$-permeable bags (XPEDX, Denver, Colo.), and incubated right side-up at 37° C. in the presence of 5–7% $CO_2$ for a period of 21 days. Afterwards, the plates were removed from the incubator and placed on the bench upside-down at room temperature for at least three hours (or overnight), to eliminate the condensate. The plates were examined without opening the polyethylene bags, using a dissecting microscope (10×). The number of colonies on each segment were counted, and the number of colonies on drug-containing segments was compared with that on the drug-free control.

Laboratory strains (QC): *M. tuberculosis* $H_{37}Rv$ susceptible to all antituberculosis drugs (ATCC #27294), and *M. tuberculosis* mono-resistant to PZA (ATCC #35828). Two PZA-resistant mutants were developed from pansusceptible strains ($H_{37}Rv$ and #9719) by selection in the presence of 12 μg/ml of PZA on agar plates at pH 6.0. Fifty-five clinical isolates, reported by our clinical laboratory as susceptible (25) or resistant (30) to PZA, were tested by the BACTEC radiometric method in the pH 6.0 liquid medium, using three PZA concentrations—100,300, and 900 μg/ml (Heifets, In L. B. Heifets (ed.), Drug susceptibility in the chemotherapy of mycobacterial infections, Chapter 3, pp. 89–122, CRC Press, Boca Raton, 1991). The phenotypic assessments of the results for the 25 PZA-resistant strains was confirmed genetically by Dr. Zhang's laboratory (Scorpio et al., *Antimicrob. Agents Chemother.,* 41:540–543, 1997; Scorpio et al., *Nature Med.,* 2:662–667, 1996).

Results

The broth-determined MICs of PZA for two pansusceptible strains were ≦100 μg/ml at pH 6.0 of the standard BACTEC PZA medium. While the growth of one of these strains (9719) was completely inhibited by all drug-concentrations incorporated in the agar medium, a substantial proportion (35.9%) of another strain ($H_{37}Rv$) was not inhibited by 300 μg/ml in agar (Table 7). Growth of both PZA-resistant mutants was not inhibited by all drug-concentrations used for both media, showing full resistance to all concentrations used in the BACTEC broth (MIC>99 μg/ml). Suspensions prepared with the intention of having 10%, 25% and 50% of PZA-resistant bacteria in the mixtures of original susceptible and their resistant mutants, have shown proportions of resistant bacteria growth on the plates approximating that in the prepared mixtures. This correlation is indicative of the potential to report the proportion of the PZA-resistant bacteria in a specimen, even if such proportion is as low as 10%.

TABLE 7

Evaluation of two PZA susceptibility methods using artificial mixtures of resistant mutants with the original strain

| % of resistant bacteria incorporated | Proportions (%%) of resistant bacteria as determined by agar plates containing the drug (μg/ml) 300 | 900 | 1200 | MIC (μg/ml) Agar | BACTEC |
|---|---|---|---|---|---|
| | | a) strain $H_{37}Rv$ | | | |
| 0 | 35.9 | 0.7 | 0 | 900 | <100 |
| 10 | 42.7 | 23.8 | 18.9 | >1200 | >900 |
| 25 | 42.6 | 26.6 | 23.9 | >1200 | >900 |
| 50 | 57.0 | 78.5 | 43.5 | >1200 | >900 |
| 100 | 98.6 | 74.1 | 96.3 | >1200 | >900 |
| | | b) strain 9719 | | | |
| 0 | 0 | 0 | 0 | <300 | <100 |
| 10 | 13.8 | 8.6 | 8.6 | 900 | >900 |
| 25 | 18.1 | 16.2 | 16.5 | >1200 | >900 |
| 50 | 35.9 | 36.9 | 40.0 | >1200 | >900 |
| 100 | 97.8 | 96.1 | 86.2 | >1200 | >900 |

The results of the test in agar medium supplemented with bovine calf serum were compared with that of the BACTEC method using different PZA concentrations. Table 8a analyzes the results for 900 and 122 μg/ml in agar medium vs 300 or 900 μg/ml in the BACTEC medium. This analysis indicated 100% agreement for 25 PZA-susceptible strains tested with either 900 or 1200 μg/ml incorporated in the agar medium. From a total of 30 strains identified as resistant to 300 μg/ml by the BACTEC method, resistance to PZA in agar medium was observed for 29 strains with a concentration of 900 μg/ml (96.7%) and for 27 strains with 1200 μg/ml (90%).

When the breakpoint of 900 μg/ml has been used in the BACTEC system (Table 8b), the agreement in results for susceptible strains was 92.9% (26 of 28 strains) or 96.4% (27 of 28 strains). Detection of resistance by this approach was slightly better than in the previous setting (Tables 8a and 8b).

TABLE 8

Comparison of the results of testing 55 *M. tuberculosis* clinical isolates with PZA by two methods

| | Number of strains by the agar proportion method: 900 μg/ml Susceptible | 900 μg/ml Resistant | 1200 μg/ml Susceptible | 1200 μg/ml Resistant |
|---|---|---|---|---|
| | a) Comparison with 300 μg/ml in BACTEC | | | |
| By the BACTEC 300 μg/ml | | | | |
| Susceptible | 25 | 0 | 25 | 0 |
| Resistant | 1 | 29 | 3 | 27 |
| | b) Comparison with 900 μg/ml in BACTEC | | | |
| By the BACTEC 900 μg/ml | | | | |
| Susceptible | 26 | 2 | 27 | 1 |
| Resistant | 0 | 27 | 1 | 26 |

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An agar medium, comprising:

a. an agar base suitable for growth of *Mycobacterium tuberculosis*; and, b. animal serum at a concentration of between about 8% and 12% of the final volume of the agar medium;

wherein said medium is at a pH of between about 6.0 to about 6.25.

2. The agar medium of claim 1, wherein said agar base is selected from the group consisting of Middlebrook and Cohn 7H10 and Middlebrook and Cohn 7H11.

3. The agar medium of claim 1, wherein said animal serum is selected from the group consisting of bovine fetal calf serum, calf serum, bovine serum, equine fetal calf serum and equine serum.

4. The agar medium of claim 1, wherein said animal serum is at a concentration of between about 9% and 11% of the final volume of the agar medium.

5. The agar medium of claim 1, wherein said animal serum is at a concentration of about 10% of the final volume of the agar medium.

6. The agar medium of claim 1, wherein said medium is at a pH of between about 6.1 and 6.2.

7. The agar medium of claim 1, wherein said medium is at a pH of about 6.1.

8. The agar medium of claim 1, wherein said medium further comprises a mixture of antimicrobial agents comprising polymixin B, carbenicillin, amphotericin B, and trimethoprim lactate.

9. The agar medium of claim 8, wherein said antimicrobial agents are present at a final concentration of: 200 units/ml polymyxin B, 10 μg/ml amphotericin B, 50 μg/ml carbenicillin, and 20 μg/ml trimethoprim.

10. The agar medium of claim 1, wherein said medium further comprises an amount of at least one drug effective for the identification of Mycobacterium tuberculosis organisms that are susceptible or resistant to said drug.

11. The agar medium of claim 10, wherein said at least one drug is selected from the group consisting of: isoniazid, streptomycin sulfate, di-hydro-streptomycin, rifampin, pyrazinamide, ethambutol, etionamide, capreomycin sulfate, amikacin, kanamycin sulfate, levofloxacin, p-aminosalicylic acid, D-cycloserine, and clofazimine.

12. The agar medium of claim 1, wherein said medium further comprises the drugs isoniazid and rifampin, and wherein each of said drugs is isolated within a segment of said agar medium.

13. The agar medium of claim 12, wherein said isoniazid is present in two segments of said agar medium, and wherein each segment contains a different concentration of said isoniazid.

14. The agar medium of claim 1, wherein said medium further comprises the following drugs: isoniazid, rifampin, pyrazinamide and either of streptomycin sulfate or di-hydro-streptomycin, and wherein each of said drugs is isolated within a different segment of said agar medium.

15. The agar medium of claim 1, wherein said medium further comprises the following drugs: ethambutol, etionamide, levofloxacin, capreomycin sulfate, and either of amikacin or kanamycin sulfate, and wherein each of said drugs is isolated within a different segment of said agar medium.

16. The agar medium of claim 1, wherein said medium further comprises the following drugs: p-aminosalicylic acid, D-cycloserine, and clofazimine, and wherein each of said drugs is isolated within a different segment of said agar medium.

17. The agar medium of claim 10, wherein said at least one drug comprises pyrazinamide.

18. A method for culturing *Mycobacterium tuberculosis*, comprising inoculating an agar medium with a sample containing *Mycobacterium tuberculosis*, wherein said agar medium comprises:

a. an agar base suitable for growth of *Mycobacterium tuberculosis*; and, b. animal serum at a concentration of between about 8% and 12% of the final volume of the agar medium;

wherein said medium is at a pH of between about 6.0 to about 6.25.

19. The method of claim 18, wherein said medium further comprises a mixture of antimicrobial agents comprising polymixin B, carbenicillin, amphotericin B, and trimethoprim lactate.

20. The method of claim 19, wherein said antimicrobial agents are incorporated into one half of said agar medium in a plate, and wherein the other half of said agar medium in said plate does not contain said antimicrobial agents.

21. The method of claim 18, wherein said agar medium is inoculated with an undiluted sample obtained from a patient.

22. The method of claim 18, wherein said sample is diluted by at least about 10 fold.

23. The method of claim 18, wherein said sample is a previously isolated sample of *Mycobacterium tuberculosis*.

* * * * *